United States Patent
Bianchi et al.

(10) Patent No.: US 10,563,270 B2
(45) Date of Patent: Feb. 18, 2020

(54) SOLID FORMS OF MENAQUINOLS

(71) Applicant: Gnosis S.p.A., Milan (IT)

(72) Inventors: Davide Bianchi, Desio (IT); Simona Daly, Desio (IT); Niccolo Miraglia, Desio (IT); Antonella Trentin, Desio (IT); Federica Colzani, Desio (IT); Francesca Bollini, Desio (IT); Cesare Ponzone, Desio (IT)

(73) Assignee: Gnosis S.p.A., Milan (IT)

( * ) Notice: Subject to any disclaimer, the term of this patent is extended or adjusted under 35 U.S.C. 154(b) by 31 days.

(21) Appl. No.: 15/558,871

(22) PCT Filed: Mar. 18, 2016

(86) PCT No.: PCT/IB2016/051528
§ 371 (c)(1),
(2) Date: Sep. 15, 2017

(87) PCT Pub. No.: WO2016/151447
PCT Pub. Date: Sep. 29, 2016

(65) Prior Publication Data
US 2018/0066326 A1    Mar. 8, 2018

(30) Foreign Application Priority Data

Mar. 20, 2015    (IT) .................... 102015009450

(51) Int. Cl.
| C12R 1/07 | (2006.01) |
| A61K 31/05 | (2006.01) |
| C07C 37/07 | (2006.01) |
| C07C 37/84 | (2006.01) |
| C07C 39/225 | (2006.01) |
| C12P 7/22 | (2006.01) |
| C12R 1/185 | (2006.01) |
| C12R 1/38 | (2006.01) |

(52) U.S. Cl.
CPC ............... *C12R 1/07* (2013.01); *A61K 31/05* (2013.01); *C07C 37/07* (2013.01); *C07C 37/84* (2013.01); *C07C 39/225* (2013.01); *C12P 7/22* (2013.01); *C12R 1/185* (2013.01); *C12R 1/38* (2013.01)

(58) Field of Classification Search
CPC ....................................... A61K 31/05
USPC ........................ 514/728, 731, 732
See application file for complete search history.

(56) References Cited

FOREIGN PATENT DOCUMENTS

| EP | 2060256 A1 | 5/2009 |
| JP | 2003137716 | 5/2003 |
| JP | 2006083132 | 3/2006 |

OTHER PUBLICATIONS

Naohiro et al., English Machine Translation of JP 2006-083132A, 15 pages (Year: 2006).*
New World Encyclopedia, "Room Temperature" http://www.newworldencyclopedia.org/entry/Room_temperature, accessed Oct. 29, 2018, 4 pages. (Year: 2018).*

* cited by examiner

*Primary Examiner* — Kevin E Weddington
(74) *Attorney, Agent, or Firm* — Amin Talati Wasserman LLP; George M. Carrera, Jr.

(57) ABSTRACT

Disclosed are solid forms of menaquinol and processes for obtaining them by chemical or enzymatic reduction of menaquinone. Said solid forms possess high stability to oxidation which allows effective use of menaquinol in the most common formulations wherein vitamin K2 is used.

7 Claims, 6 Drawing Sheets n = 1-11

SOLID FORMS OF MENAQUINOLS

FIELD OF INVENTION

The present invention relates to solid forms of menaquinols (the reduced form of menaquinones) characterized by particularly high stability to oxidation, thus allowing their real, effective use in the prevention of cardiovascular disorders, in bone metabolism and in inflammatory processes involving vitamin K.

BACKGROUND TO THE INVENTION

Menaquinones are a family of molecules which, as a whole, constitute the components of vitamin K2.

In their most common oxidized form, menaquinones have general formula (I):

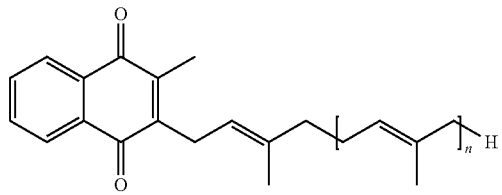

(I)

wherein n is 0 or an integer between 1 and 11.

They differ in terms of the number of isoprene units (the part of the molecule shown in brackets in formula I), the number of which can range from 0 to 11, although the most common forms range from 4 to 7 and relate to menaquinone-4 (MK-4), MK-5, MK-6 and MK-7 respectively. Menaquinones MK-4 and MK-7 are the most plentiful, and are the two available on the diet products market.

The main food sources of vitamin K2 are eggs, dairy products, liver and fermented soya.

The therapeutic use of vitamin K, and especially that of vitamin K2, is described in several patents and scientific publications, with applications ranging from the cardiovascular field (M. K. Shea et al., Am. J. Clin. Nutr. (2009) 89: 1-9) to bone metabolism (M. H. J. Knapen et al., Osteoporos Int (2013) 24:2499-2507). More recent applications of vitamin K relate to the field of inflammation (M. K. Shea et al., Am J Epidemiol. (2008); 167(3): 313-320).

However, the intestinal absorption of the various forms of vitamin K following oral intake, either in food or as a diet supplement, is not very high due to the strongly lipophilic nature of the molecule.

The administration of vitamin K2 in its reduced form of menaquinol, a much more hydrophilic molecule, is believed to increase the absorption of the vitamin, as already demonstrated for a structurally similar molecule, ubiquinol, the reduced form of ubiquinone (M. Evans et al., J. Funct. Foods (2009) 1(2); 240).

The menaquinols are represented by the following general formula (II):

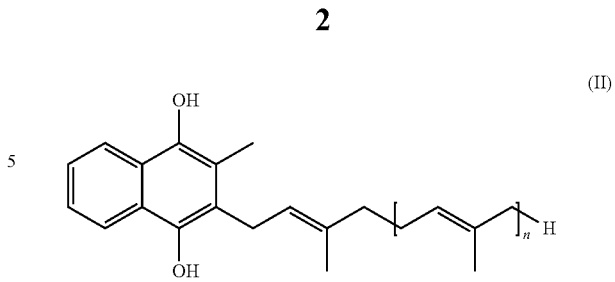

(II)

wherein N is as defined above.

However, menaquinols are highly unstable and tend to reoxidise very quickly to menaquinones under the effect of atmospheric oxygen or mild oxidizing agents. The stability of the reduced form of vitamin K2 is difficult to guarantee even in an inert oxygen-free environment, as in the case of the isolated dried solid, stored sealed in a nitrogen atmosphere.

Pharmaceutical and nutraceutical compositions containing menaquinol of formula (II) as active ingredient are described in EP 2060256 A1, wherein menaquinol is prepared by reducing a solution of menaquinone in an organic solvent with an aqueous solution of reducing agent, followed by separation of the phases and recovery of menaquinol from the organic phase.

DESCRIPTION OF THE INVENTION

In a first aspect, the invention relates to solid forms of menaquinol having surprising stability to oxidation, under standard conditions and crystal stress conditions, which allows effective use of menaquinol in the most common formulations wherein vitamin K2 is used.

Figure 1:
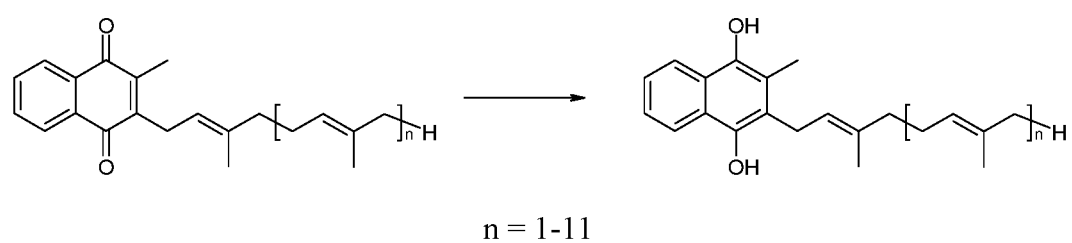
FIG. 1: Reduction of menaquinone to menaquinol.

Said forms are obtained by reducing menaquinone to menaquinol, as shown in FIG. 1.

In one embodiment of this first aspect of the invention, the solid form is a crystalline form of menaquinol of formula (II), obtained by reducing menaquinone of formula (I) with sodium dithionite followed by crystallization from water.

The reduction takes place in a biphasic system consisting of a water-immiscible solvent such as ethyl acetate, butyl acetate, methyl-tetrahydrofuran, dichloromethane or dichloroethane, preferably ethyl acetate, and of a sodium dithionite aqueous solution, preferably having a pH ranging between 3 and 8. The reduction is effected at a temperature ranging between 2° C. and 75° C., preferably between 20° C. and 25° C. The sodium dithionite concentration in the aqueous solution preferably ranges between 0.5 and 10% weight/ volume, while that in the biphasic water+solvent system preferably ranges between 1/10 and 1/100, said ratios being the ratios between the weight of the vitamin and the total volume (solvent+water).

At the end of the reduction the solvent is removed by evaporation, preferably by low-pressure evaporation, to give an aqueous suspension containing the solid, wherein the ratio between solid and water can range from 1/5 to 1/100, and the menaquinol crystallizes from the aqueous phase, by cooling to a temperature below 25° C., preferably to a temperature between 2° C. and 8° C., most preferably between 2° C. and 4° C.

The solid crystalline form of menaquinol according to the invention is then isolated by filtration, operating at the same temperatures as for the crystallization.

Filtration can be followed by washing of the solid with 1 to 10% solutions of ascorbic acid and final drying at a temperature not exceeding 40° C.

The crystallization can be conducted in the absence of other salts or in the presence of up to 1 M of NaCl dissolved in the aqueous phase.

The crystalline form of menaquinol (II) thus obtained can be recrystallized by dissolving in ethanol and recrystallising by adding an aqueous solution of ascorbic acid at a temperature below 25° C., preferably at a temperature ranging between 2° C. and 8° C., and even more preferably between 2° C. and 4° C.

In a particular embodiment of said first aspect of the invention, the crystalline form of menaquinol relates both to menaquinol 7 (compound of formula (II) wherein n=6) and menaquinol 4 (compound of formula (II) wherein n=3).

Figure 4:
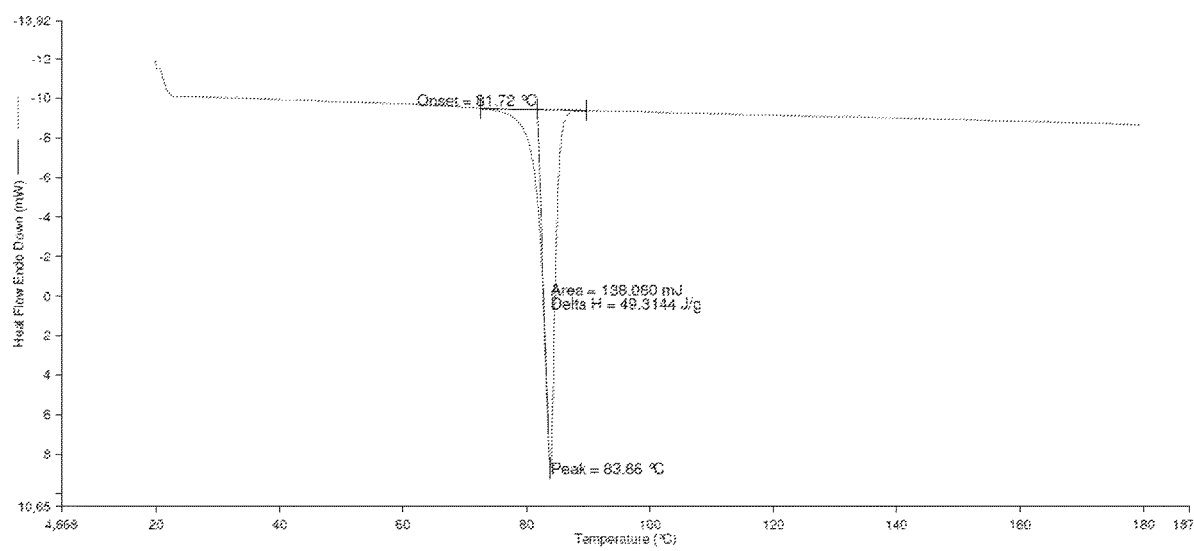
FIG. 4: DSC thermogram of a reduced vitamin K2-(MK7) sample (high-melting polymorph) obtained according to Example 2.
Figure 5:
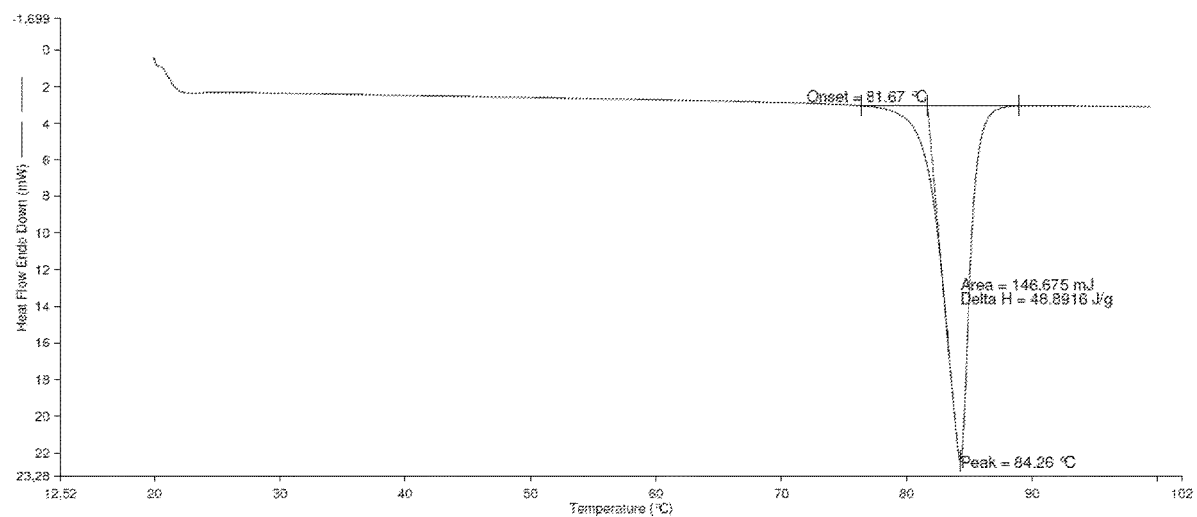
FIG. 5: DSC thermogram of a reduced vitamin K2-(MK7) sample (high-melting form) after recrystallization according to Example 6.
Figure 6:
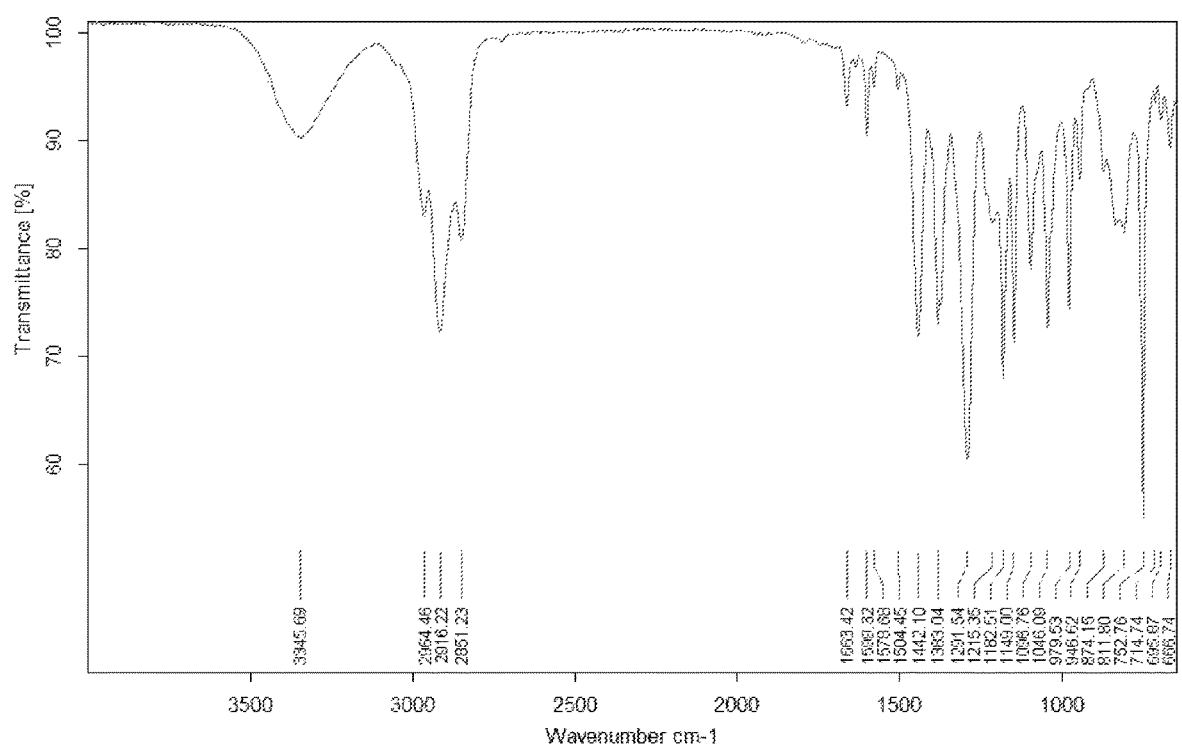
FIG. 6: FTIR spectrum of a reduced crystalline vitamin K2-(MK7) sample obtained according to Example 2 or 6.

In particular, the invention relates to a reduced crystalline form of menaquinol 7 having a DSC profile wherein an endothermic peak is present at a temperature equal to or greater than 75° C., as shown, for example, in FIG. 4, and an FTIR spectrum as shown in FIG. 6, wherein typical absorption bands are present: broad peak at 3340-3350 cm-1, three typical bands at 2964, 2916, 2851; sharp peaks at 1599, 1504, 1326, 1182, 1149, 1096, 1046, 980, 950 and 752 cm$^{-1}$.

Figure 3:
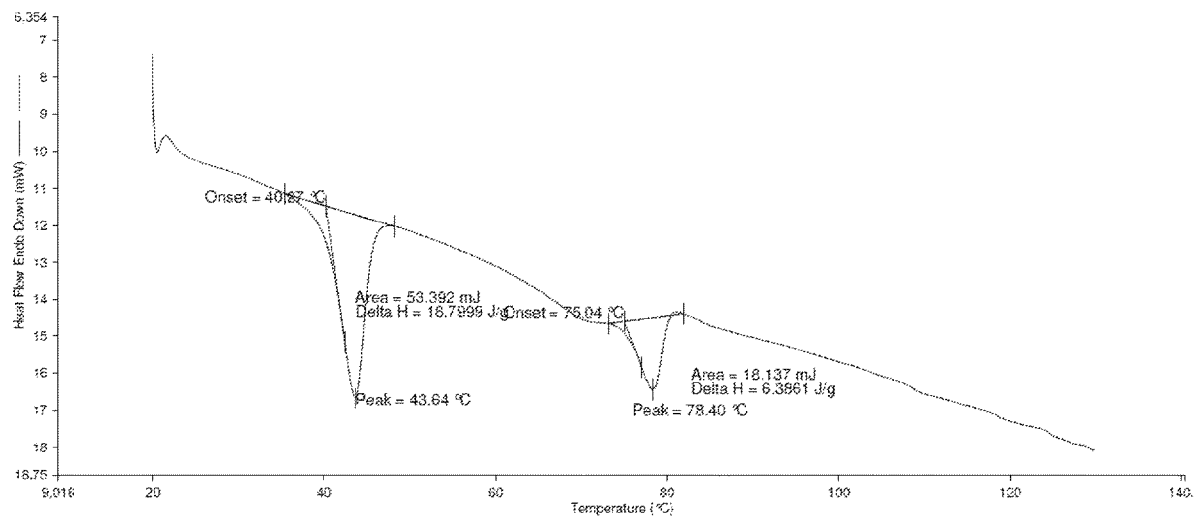
FIG. 3: DSC thermogram recorded on a sample of reduced vitamin K2-(MK7) (polymorphic forms) obtained in accordance with Examples 3, 4 and 5.

The invention also relates to a mixture of polymorphic forms of menaquinol 7 obtained by reducing menaquinone 7 having a DSC profile with an endothermic peak at a temperature equal to or greater than 78.4° C. and a second endothermic event in the 39-45° C. range, as shown, for example, in FIG. 3.

In another embodiment of said first aspect of the invention, the solid form of menaquinol of formula (II) is obtained by enzymatically reducing menaquinone of formula (I).

Cell suspensions of a micro-organism of the genus *Bacillus* can be used for this purpose; in particular said micro-organism can be selected from *Bacillus subtilis, Bacillus stearothermophilus, Bacillus amyloliquefaciens, Bacillus megaterium, Bacillus pumilus* and *Bacillus licheniformis*, or of the genus *Pseudomonas*, in particular *Pseudomonas putida*; or the genus *Escherichia*, in particular of the species *Escherichia coli*; or the genus *Enterobacter*, in particular *Enterobacter aerogenes*, prepared by conventional methods. Typically, the cells of the micro-organisms are grown in a suitable culture medium, such as LB 2× supplemented with glucose at the concentration of 2-6 g/l, at 28-37° C. At the end of the growth the culture broth is centrifuged and the cells are washed with phosphate buffer pH 7.4 and resuspended in phosphate buffer pH 7.4 with the addition of 0.5-2.5 g/l of sodium succinate and 2-6 g/l of glucose, to obtain a cell suspension at the final concentration of 5-15 g/l.

The enzymatic reduction is typically conducted by mixing four volumes of the cell suspension thus obtained, preferably at the concentration of 10 g/l, with one volume of a solution of menaquinone in a water-miscible solvent, typically at the concentration of 0.6-1.4 g/l. The water-miscible solvent is preferably selected from the group of ethanol, methanol, isopropanol, acetone, THF, methyl-THF, dimethylformamide, dimethylacetamide and dimethylsulphoxide. The reaction mixture thus prepared is incubated at 28-32° C., preferably at 30° C., under stirring, protected from the light, typically for an incubation time ranging between 2 and 12 hours, depending on the cell concentration used. At the end of the incubation the reaction mass, containing the solid form of menaquinol according to the invention, is frozen and freeze-dried.

The lyophilisates thus obtained can be resuspended in a biphasic mixture containing water and at least one of the water-immiscible organic solvents previously described, filtered, and said filtrates recovered by crystallization as previously described and further illustrated in example 2.

Alternatively, the reaction mass containing reduced vitamin K2 can be filtered, diluted in a biphasic mixture containing water and at least one of the water-immiscible organic solvents previously described, and recovered by crystallization as previously described and illustrated in example 2.

The invention also relates to pharmaceutical or nutraceutical compositions containing the solid forms described.

The invention also relates to the use of the solid forms described above to prepare medicaments for the treatment and/or prevention of cardiovascular and bone metabolism disorders, and inflammatory states involving vitamin K.

The reduced solid forms of general formula (II) according to the invention possess greater bioavailability than the corresponding menaquinones of general formula (I), as suggested by in vitro absorption experiments conducted on a monolayer of Caco-2 cells.

The invention is further illustrated by the following examples.

Example 1 (Comparative): Obtaining Reduced Amorphous Vitamin K2-(MK7)

0.25 g of vitamin K2-(MK7) with an assay value >97% is dissolved under nitrogen in 20 ml of THF. 0.26 g of zinc is added to said solution, and the reaction mass, maintained under nitrogen, is heated to reflux. The solution is analyzed by HPLC to ensure that the vitamin has been completely reduced. After 23 h the reaction mass is filtered to allow the removal of the zinc powder, and the filtrate is concentrated to dryness in situ, under vacuum. This process affords 0.26 g of a pale pink oil that tends to solidify in time, forming a waxy solid. HPLC analysis shows a chromatographic purity relating to vitamin K2-(MK7) reduced by 96.5% (oxidized=3.5%).

The corresponding stability tests are set out in Table 1.

TABLE 1

Stability data of a sample of low-melting polymorph (amorphous sample) of vitamin K2-(MK7). The data are expressed as a percentage of the initial value of the reduced form

| Time (days) | Reduced ($t/t_0$ %) |
| --- | --- |
| 0 | 100% |
| 3 | 4% |

Figure 2:
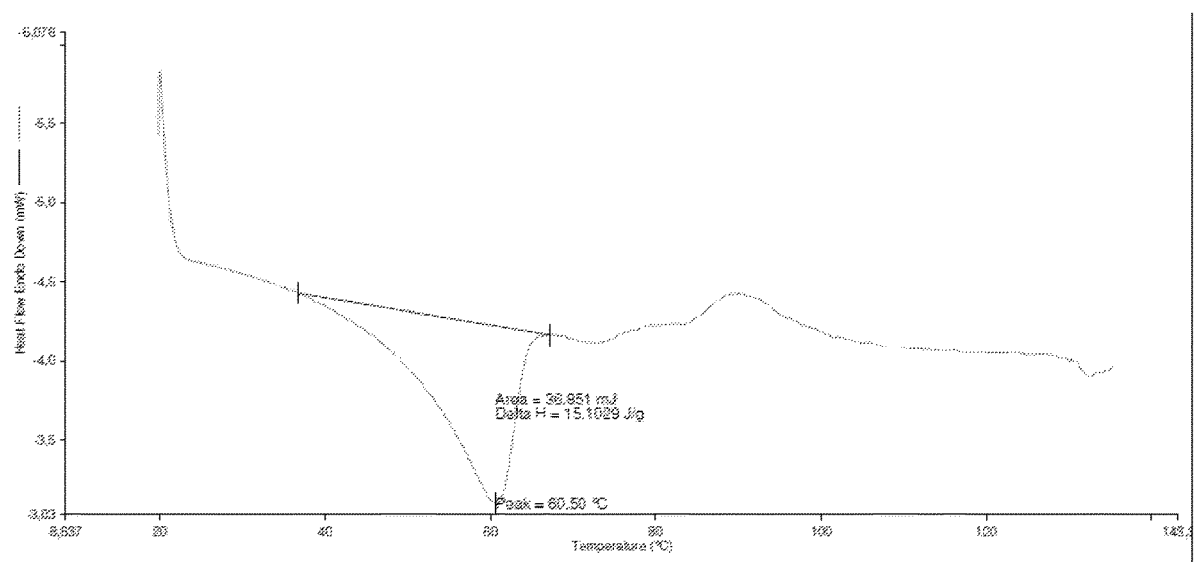
FIG. 2: DSC thermogram of the amorphous form of reduced vitamin K2-(MK7) obtained according to Example 1.

FIG. 2 shows a DSC thermogram recorded on a sample of amorphous vitamin K2-(MK7), obtained according to the present example.

Example 2: Obtaining Reduced Crystalline Vitamin K2-(MK7)

5 g of vitamin K2-(MK7) with an assay value>97% is dissolved in 250 ml of ethyl acetate.

A sodium dithionite aqueous solution (250 ml, 4.76 g of sodium dithionite), corrected to pH=4 with sulphuric acid, is added to said solution, maintained under nitrogen and vigorous stirring. The solution is analyzed by HPLC to ensure that the vitamin has been completely reduced. The reaction is complete after 3 h. The reaction mass is concentrated under vacuum at 40° C. until an aqueous suspension is obtained. Said suspension is cooled to 4° C., and then filtered through a Buchner funnel; the cake is washed with a 1% aqueous solution of ascorbic acid, giving a wet solid which is dried at 40° C. under vacuum (85-10 mbar) overnight. 4 g of reduced vitamin K2-(MK7) is recovered after drying. HPLC analysis shows a chromatographic purity relating to vitamin K2-(MK7) reduced by 98.5% (oxidised=2.5%), KF=5.0%.

The stability tests are set out in Table 2.

TABLE 2 stability data of a sample of high-melting crystalline polymorph of vitamin K2-(MK7), expressed as a percentage of the initial value of the reduced form

| Packaging | T = 0 | T = 1 month | T = 2 months | T = 3 months |
|---|---|---|---|---|
| Alu/vacuum | 100% | 95.4% | 98.9% | 97.9% |

Example 3: Obtaining Reduced Vitamin K2-(MK7) (Mixture of Polymorphs)

1 g of vitamin K2-(MK7) with an assay value >97% is dissolved in 60 ml of ethyl acetate.

A sodium dithionite solution adjusted to pH=4 with sulphuric acid (60 ml of water, 2.4 g of sodium dithionite) is added to this solution, maintained under nitrogen and under vigorous stirring. The solution is analyzed by HPLC to ensure that the vitamin has been completely reduced. The reaction is complete after 3 h. The reaction mass is placed in a separator funnel and the two phases are separated, maintaining the upper phase under nitrogen. Said phase is transferred to a rotary evaporator and immediately placed under vacuum to remove the solvent until dry (40° C., 10 mbar, until an oily residue is obtained). 100 ml of an aqueous solution of ascorbic acid is added to the oily residue, and the mixture is maintained under nitrogen and under vigorous stirring for 5-30 min. at the temperature of 20-25° C. The mixture is then filtered through a Buchner funnel at room temperature (20-25° C.); the cake is washed with a 1% aqueous solution of ascorbic acid to give 0.5 g of reduced vitamin K2-(MK7). HPLC analysis shows a chromatographic purity relating to vitamin K2-(MK7) reduced by 81.6% (oxidised=18.4%).

DSC analysis reveals the presence of two endothermic peaks at 43.7° C. and 76.3° C.

Example 4: Obtaining Reduced Vitamin K2-(MK7) (Mixture of Polymorphs)

1 g of vitamin K2-(MK7) is reduced by the procedures described in Example 1. 100 ml water is added to the oily residue, maintaining the reaction mass under stirring and under nitrogen, at 20-25° C. The suspension that forms (deep pink colour) is then filtered, in nitrogen atmosphere, giving a solid corresponding to reduced vitamin K2-(MK7) (HPLC purity as vitamin K2-(MK7) 81.6%, oxidised 18.4%).

The stability tests are set out in Table 3.

TABLE 3 stability data of a sample of a mixture of polymorphic forms of vitamin K2-(MK7)

| Time (days) | % vitamin reduced | % vitamin oxidised |
|---|---|---|
| 0 | 81.58% | 18.41% |
| 3 | 76.24% | 23.67% |
| 6 | 63.16% | 36.69% |
| 10 | 48.27% | 51.48% |
| 11 | 47.04% | 52.67% |
| 12 | 38.44% | 61.09% |

DSC analysis detects the presence of two endothermic peaks at 43.6° C. and 78.4° C. (FIG. 3).

Example 5: Obtaining Reduced Vitamin K2-(MK7) (Mixture of Polymorphs)

1 g of vitamin K2-(MK7) is reduced by the procedures described in Example 2. Upon completion of the reduction the reaction mass is concentrated under vacuum (10 mbar residual, 25° C. internal), and the milky suspension formed is then filtered through a Buchner funnel and washed with a 1% solution of ascorbic acid. The resulting solid is dried under vacuum at 40° C. overnight (40° C., 5 mbar), to give 0.76 g of a pale pink solid. HPLC analysis shows a chromatographic purity relating to vitamin K2-(MK7) reduced by 93.7% (oxidised=6.3%), KF=3.0%.

DSC analysis detects the presence of two endothermic peaks at 43.7° C. and 79.8° C.

Example 6

2 g of vitamin K2-(MK7), obtained by the procedures described in Example 2 (Red Vit purity=96.5%), is dissolved in 2 ml of absolute ethanol. A 10% aqueous solution of ascorbic acid (100 ml) is added by dripping to the solution, maintained under stirring and under nitrogen, at 2-8° C.

The vitamin E thus precipitates, and the suspension that forms is then filtered, in a nitrogen atmosphere, to give a solid corresponding to vitamin K2-(MK7) (HPLC purity as vitamin K2-(MK7) 96.3%, oxidised 4.7%).

Example 7

0.3 g of vitamin K2-(MK7) is reduced by the procedures described in Example 2. At the end of the reaction the resulting solid is redissolved in ethanol (1.5 ml) and cooled to 5° C. The solid that precipitates is maintained at 5° C. under nitrogen for 12 h; the precipitate is then filtered and dried at 40° C. under vacuum, to give 0.2 g of yellowish-white solid (purity in reduced vitamin=10.7%, oxidised 88.7%).

Example 8

*Bacillus subtilis* cells were grown in LB 2× medium (casein tryptone 20 g/l, yeast extract 10 g/l, sodium chloride 10 g/l) supplemented with glucose (3 g/l) at 30° C., O/N. At the end of the growth the culture broth was centrifuged, the cells were washed with 50 mM pH 7.4 phosphate buffer and resuspended in 50 mM pH 7.4 phosphate buffer with the addition of sodium succinate (1 g/l) and glucose (5 g/l), to obtain a cell suspension at the final concentration of 10 g/l.

8 ml of the suspension was mixed with 2 ml of a solution of vitamin K2-MK7 prepared in DMSO at the concentration of 1 g/l. The reaction mixture thus prepared was fluxed with inert nitrogen and incubated at 30° C., under stirring, for 24 hours. The reduction of menaquinone to menaquinol was checked by HPLC analysis. The maximum concentration of vitamin K2-(MK7) in reduced form was detected after 4 hours' incubation, and corresponds to 93% of the menaquinone present.

At the end of incubation the reaction mass was frozen and freeze-dried.

Example 9

A reaction mass (100 ml) containing 20 mg-act of vitamin K2-(MK7), obtained according to example 8, was then filtered through a Buchner funnel to remove the biomass. The cake is washed with 20 ml of aqueous mixture containing DMSO (8/2) and combined with the preceding filtrate. 10 ml of ethyl acetate is added under nitrogen to the combined filtrate. The resulting solution is concentrated under vacuum at 5-10 mbar to give an aqueous suspension, which is cooled to 2-8° C. After 30 min. under stirring the suspension is filtered and the solid obtained is dried at 40° C., under vacuum (10 mbar residual). The HPLC analysis conducted on the solid recovered (12 mg) shows a purity of 82% in reduced vitamin and the presence of the endothermic peak (DSC) at 83.1° C.

Example 10: Absorption of Reduced or Oxidized Vitamin K2-(MK7) on Cell Monolayer of Caco-2 Cells In Vitro Caco-2 human adenocarcinoma cells were cultured on a permeable insert inserted in the well of a microplate to form a confluent monolayer with the barrier function between an apical and a basolateral compartment. The perfect integrity of the monolayer was determined by testing for the absence of passage by lucifer yellow, a compound with low permeability. Samples of vitamin K2-(MK7), alternatively in the reduced form (menaquinol) or the oxidized form (menaquinone), were dissolved in ethanol and applied to the apical compartment, the 1% ethanol solution being added to the incubation buffer. The final solution in the incubation well was fixed at 100 μM of vitamin.

At the end of the incubation period the cell layer was removed from the insert and homogenized, and the homogenate was centrifuged. The amount of vitamin present in the supernatant was determined by HPLC. The centrifugation pellet was then resuspended in 1 ml of water, and 1.5 ml of isopropanol and 2.5 ml of hexane were added to the suspension. After stirring, the organic phase formed was analyzed, again by HPLC, for the concentration of vitamin K2 (MK7). The total of the two values was used to calculate the amount of vitamin internalized by the cell layer.

The values found, expressed as μg of vitamin per g of homogenate, indicate a slightly but significantly higher uptake in the case of application of vitamin K2 (MK7) in reduced form, as shown in Table 4.

TABLE 4 absorption of reduced or oxidised vitamin K2-(MK7) on cell monolayer of Caco-2 cells in vitro

| Incubation | Reduced vitamin μg/g hom. | Oxidised vitamin μg/g hom. |
|---|---|---|
| well 1 | 0.8 | 0.4 |
| well 2 | 1.6 | 0.5 |
| well 3 | 1.0 | 0.6 |
| well 4 | 0.8 | 0.7 |
| mean | 1.1 | 0.6 |
| SD | 0.4 | 0.1 |

The invention claimed is:

1. A process for the preparation of a crystalline form of menaquinol of formula (II)

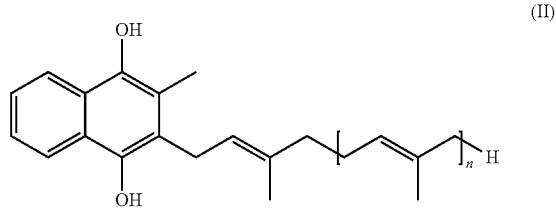

(II)

wherein n is 0 or an integer from 1 to 11, comprising the following steps:

a) reducing menaquinone of formula (I)

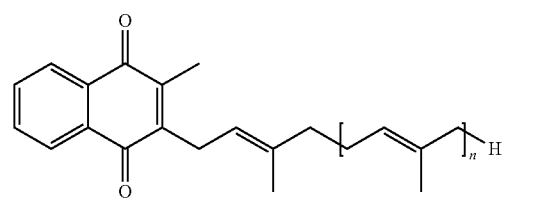

(I)

wherein n is as defined above, in a biphasic system consisting of a water-immiscible solvent and an aqueous solution of sodium dithionite;

b) removing said solvent by evaporation to provide an aqueous phase;

c) Cooling and filtering the aqueous phase obtained in step b) at a temperature lower than 25° C., to give a crystalline form of menaquinol of formula (II).

2. The process of claim 1 wherein step a) is performed at a temperature between 2° C. and 75° C.

3. The process of claim 1 wherein the solution of sodium dithionite has a pH ranging between 3 and 8.

4. The process of claim 1, further comprising washing of the crystalline form obtained in step c) with a solution of ascorbic acid followed by drying of the crystals at a temperature not exceeding 40° C.

5. The process of claim 1 wherein, in the compound of formula (II), n is 6.

6. The process of claim 1 wherein, in the compound of formula (II), n is 3.

7. A pharmaceutical or nutraceutical composition containing the product obtained from the process of claim 1 and a carrier.

* * * * *